US012594234B2

(12) United States Patent
Claypool et al.

(10) Patent No.: US 12,594,234 B2
(45) Date of Patent: Apr. 7, 2026

(54) USE OF AN EPILOBIUM FLEISCHERI EXTRACT

(71) Applicant: DSM IP ASSETS B.V., Heerlen (NL)

(72) Inventors: Joshua Claypool, Kaiseraugst (CH); Dominik Imfeld, Kaiseraugst (CH); Riccardo Sfriso, Kaiseraugst (CH)

(73) Assignee: DSM IP ASSETS B.V., Maastricht (NL)

( * ) Notice: Subject to any disclaimer, the term of this patent is extended or adjusted under 35 U.S.C. 154(b) by 516 days.

(21) Appl. No.: 18/026,681

(22) PCT Filed: Sep. 17, 2021

(86) PCT No.: PCT/EP2021/075559
§ 371 (c)(1),
(2) Date: Mar. 16, 2023

(87) PCT Pub. No.: WO2022/063685
PCT Pub. Date: Mar. 31, 2022

(65) Prior Publication Data
US 2023/0346686 A1      Nov. 2, 2023

Related U.S. Application Data

(60) Provisional application No. 63/093,438, filed on Oct. 19, 2020, provisional application No. 63/083,344, filed on Sep. 25, 2020.

(30) Foreign Application Priority Data

Oct. 16, 2020      (EP) ...................................... 20202290

(51) Int. Cl.
*A61K 8/9789*      (2017.01)
*A61Q 17/00*      (2006.01)

(52) U.S. Cl.
CPC ............ *A61K 8/9789* (2017.08); *A61Q 17/00* (2013.01)

(58) Field of Classification Search
None
See application file for complete search history.

(56) References Cited

U.S. PATENT DOCUMENTS

| | | | |
|---|---|---|---|
| 2017/0209364 A1 | 7/2017 | Pawlus et al. | |
| 2020/0222358 A1 | 7/2020 | Sajic et al. | |

FOREIGN PATENT DOCUMENTS

| | | | | |
|---|---|---|---|---|
| CA | 2386648 A1 | 11/2003 | | |
| CN | 105816498 A | 8/2016 | | |
| CN | 107157881 A | 9/2017 | | |
| CN | 110 711 148 | 1/2020 | | |
| DE | 102007024381 A1 | 3/2008 | | |
| FR | 2 918 882 | 1/2009 | | |
| WO | WO-2009010587 A1 * | 1/2009 | .............. | A61P 31/04 |
| WO | 2019/173782 | 9/2019 | | |
| WO | 2004/016236 A1 | 2/2024 | | |

OTHER PUBLICATIONS

English language translation of WO 2009/010587 A1, Publ. Jan. 22, 2009. (Year: 2009).*
International Search Report for PCT/EP2021/075559, mailed Jan. 4, 2022, 4 pages.
Written Opinion of the ISA for PCT/EP2021/075559, mailed Jan. 4, 2022, 7 pages.
"Product Selection Guide—Innovative actives for personal care and beauty", Jan. 1, 2010 (Jan. 1, 2010), pp. 1-8, XP055099681.
"DSM Alpaflor Range. Data sheet", DSM Nutritional Products, Jan. 1, 2013 (Jan. 1, 2013), pp. 1-12, XP009501995.
Chinese Office Action issued Jun. 17, 2025 in corresponding Chinese Patent Application No. 202180064899.1.
Inventory of Used Cosmetic Ingredients (2021 Edition), Explanation, Serial No. 02353, NMPA, Apr. 27, 2021, 545 pages.

* cited by examiner

*Primary Examiner* — Dominic Lazaro
(74) *Attorney, Agent, or Firm* — NIXON & VANDERHYE P.C.

(57) ABSTRACT

The present invention relates to an Epilobium extract, preferably an Epilobium fleischeri extract for use as a prebiotic.

21 Claims, No Drawings

USE OF AN EPILOBIUM FLEISCHERI EXTRACT

This application is the U.S. national phase of International Application No. PCT/EP2021/075559 filed Sep. 17, 2021, which designated the U.S. and claims priority to EP patent application No. 20202290.1 filed Oct. 16, 2020, and which claims the benefit of U.S. Application No. 63/093,438 filed Oct. 19, 2020, and U.S. Application No. 63/083,344 filed Sep. 25, 2020, the entire contents of each of which are hereby incorporated by reference.

The present invention relates to an Epilobium extract such as preferably an Epilobium Fleischeri extract for use as a prebiotic.

Skin is the outermost protective covering of living beings and is the largest organ in the body. It acts as a barrier and protects the body from external factors. It is furthermore well known that the surface of the skin is colonized by a great variety of microorganisms which form the skin microbiome (often also called skin microbiota). Resident microbiota are found in the upper parts of the epidermis and congregated in and around the hair follicle. The majority of the microorganisms on human skin are bacteria that provide a benefit to the host (commonly referred to as commensals or good bugs). Such commensals generally live in peaceful coexistence with the host while benefiting from the sheltered ecological niche. However, the microbiota may also include or be exposed to harmful or potentially harmful bacteria (bad bugs, also referred to pathogenic microbes) such as *Staphylococcus aureus* (*S. aureus*), *Corynebacterium tuberculostearicum* (*C. tuberculostearicum*) and *Corynebacterium kroppenstedtii*, the latter two being part of a group of opportunistic bacteria defined as "coryneforms" increasingly implicated in significant infections. Pathogenic microbes are occasionally harmful to their host whilst being present on the skin, in particular if their presence exceeds certain thresholds. However, upon entry in to the human body through e.g. ingestion and through cuts in the skin, these bacteria may definitely become harmful. Thus, any disruption in the balance between the good and the bad bugs is an opportunity when a disease can set in. Therefore, obtaining and maintaining microbiome balancing, i.e. maintaining a surface of the human body, e.g. skin, in healthy and infection free condition, is often desired by people.

Microbiome balancing may be achieved e.g. by reducing bad bugs through an application of topical compositions comprising one or more antimicrobial compounds. However, most antimicrobial compounds if not all; contained in such topical compositions, do not work in a selective manner. In other words, antimicrobial compounds do not selectively act only against bad bugs but they also act on good bugs. Thus, usage of such topical compositions often leads to depletion in number of good bugs which is not desired. Furthermore such antibiotic compounds may foster antibiotic resistances which are highly unwanted.

Bacteria known to have a good effect on skin health are *Staphylococcus hominis, Staphylococcus epidermidis; Micrococcus yunnanensis; Corynebacterium granulosum, Corynebacterium accolens.*

*Staphylococcus hominis* has been shown to produce hominicin, a bacteriocin with potent activity against clinically relevant strains of *Staphylococcus aureus*, including MRSA.

*Staphylococcus epidermidis* is a generally well known skin commensal. Current research repeatedly confirms that this bacterium is an important component of a healthy microbiome and also takes over a beneficial role in acne by limiting pathogenic *C. acnes* over-colonisation and inflammation.

*Corynebacterium accolens* is able to hydrolyze skin surface triacylglycerides in vivo releasing antipneumococcal free fatty acids. *C. accolens* thus plays a beneficial role in sculpting the human microbiome.

*Corynebacterium granulosum*, as part of the skin microbiota, *C. granulosum* is found in sebum-rich areas but at a much lower abundance than Cutibacterium *acnes*. Since *C. granulosum* co-localizes with *C. acnes* in the stratum corneum and hair follicles, there it is believed that *C. acnes* competes with *C. granulosum*. The skin microbiota of papulopustular rosacea patients was reported to be depleted in *C. granulosum*, which suggests that this species may play an important role in maintaining the normal skin barrier by averting the growth of potential pathogens. It has also been shown that *C. granulosum* is able to stimulate the host immune system.

*Micrococcus yunnanensis* is part of the *M. luteus* group. *M. luteus* is a non-pathogenic species. They can also be used to detox or biodegrade environmental pollutants On the other hand microbes that are known to have negative impact on skin health are *Staphylococcus capitis; Corynebacterium tuberculostearicum; Lawsonella clevelandensis, Staphylococcus aureus* and *C. kroppenstedtii.*

*Staphylococcus aureus* is well known skin pathogen mostly associated with the occurrence of atopic dermatitis.

*Staphylococcus capitis* is a commensal, in particular on head and scalp skin and has affinity to sebaceous glands nut is also known as an opportunistic pathogen and presumed to be involved in acne formation.

*Corynebacterium tuberculostearicum* is a lipophilic species. Lipophilic corynebacteria are a particularly relevant subgroup since they might be involved in infections of hospitalized patients and often show multiresistance to antimicrobials. *C. tuberculostearicum* is stated to play a key role for inflammatory skin conditions since in skin cells as it has been shown to trigger the inflammatory cascade via nf-kappaB.

*Lawsonella clevelandensis* recently discovered and is part of the commensal flora of the skin. Common in adult nostrils (nostril microbiome it is likely a bacterium of low virulence). However, the occurrence of infections with *L. clevelandensis* is probably underestimated by routine microbiology methods as it has been observed in the formation of different type of abscess.

*Corynebacterium kroppenstedtii* is considered as an opportunistic pathogen and associated with skin redness, inflammatory dermatoses and rosacea.

Based on the different role and properties of the individual microbes as part of the microbiome this generates the need for a well-balanced and healthy composition. Certain mechanisms in the human body contribute to microbiome balancing. For example, keratinocytes, one of the major cell types that is abundantly present in a surface of the human body, e.g. skin, are known to secrete antimicrobial peptides (natural defense system) which primes skin against an attack from bad bugs.

Microbiome balancing may however also be achieved or supported by way of utilizing a prebiotic that promotes the growth of good bugs over bad bugs. Usage of a prebiotic thus leads to increase in benefits obtained from good bugs. Good bugs are said to provide benefit to their host through e.g. competing with bad bugs for availability of nutrients and through secretion of metabolites.

'Epilobium extracts' such as 'Epilobium Fleischeri extract' are cosmetic ingredients used for the regulation of sebum and the treatment of oily skin and the reduction of *C. acnes* in vitro. However nothing is known about its effect on other, such as in particular commensal skin microbes and potentially pathogenic microbes.

It has now surprisingly been found that the use of an Epilobium Fleischeri extract when applied to a surface of the human body, provides microbiome balancing. It has also been found that the microbiome balancing so obtained is by way of Epilobium Fleischeri extract functioning as a prebiotic, i.e. it preferentially promotes growth of good bacs over bad bugs.

The benefit of microbiome balancing could take place through various mechanisms and it is not necessary that every substance that provides microbiome balancing does so by way of the substance being a prebiotic. The invention in the present application is by way of a finding that Epilobium extracts such as preferably an Epilobium fleischeri extract behaves as a prebiotic which, to the knowledge of the present inventors, has not been known heretofore.

Thus, in a first aspect, the present invention relates to use of an Epilobium extract, preferably an Epilobium fleischeri extract as a prebiotic when applied to an external surface of the human body.

The prebiotic effect is characterized by Epilobium extract, preferably an Epilobium fleischeri extract promoting the growth of good bugs, such as preferably the growth of at least one, preferably all of *Staphylococcus hominis, Staphylococcus epidermidis; Micrococcus yunnanensis*; Cutibacterium *granulosum, Corynebacterium accolens* over the growth of bad bugs such as preferably over at least one, preferably all of *Staphylococcus capitis; Corynebacterium tuberculostearicum; Lawsonella clevelandensis, Staphylococcus aureus* and *C. kroppenstedtii* in the skin microbiome compared to a non-treated control, i.e. a control which has not been treated with the Epilobium extract, preferably the Epilobium fleischeri extract.

In another aspect, the present invention relates to Epilobium extract, preferably Epilobium fleischeri extract for use in providing microbiome balancing when applied on a surface of the human body.

The microbiome balancing so obtained is through Epilobium extract, preferably Epilobium fleischeri extract functioning as a prebiotic as said Epilobium extract, preferably Epilobium fleischeri extract has been found to preferentially promote growth of good bugs, such as preferably the growth of at least one, preferably all of *Staphylococcus hominis, Staphylococcus epidermidis; Micrococcus yunnanensis*; Cutibacterium *granulosum, Corynebacterium accolens* over the growth of bad bugs such as preferably over at least one, preferably all of *Staphylococcus capitis; Corynebacterium tuberculostearicum; Lawsonella clevelandensis, Staphylococcus aureus* and *C. kroppenstedtii* in the skin micorbiome.

The term Epilobum extract as used herein encompasses Epilobum extracts from any Epilobium species such as preferably from Epilobium fleischeri, Epilobium *Parviflorum* and/or Epliobium *Angustifolium* obtained from extraction of the respective Flowers, Leaves and/or Stems.

Suitable extracts encompass in particular Epilobium fleischeri and Epilobium *Angustifolium* extracts. Most preferred in all embodiments of the present invention is an Epilobium fleischeri extract with all the definitions and preferences as given herein.

The Epilobium fleischeri extract according to the present invention is obtained by the extraction of the Flowers/Leafs and Stems of the plants and is commercially available as ALPAFLOR® ALPO-SEBUM from DSM Nutritional products.

An Epilobium *Angustifolium* Extract suitable for the purpose according to the present invention is commercially available as Defenscalp™ from Lucas Meyer Cosmetics.

An Epilobium *Parviflorum* Extract suitable for the purpose according to the present invention is commercially available from Kingherbs.

Preferably, in all embodiments of the present invention the Epilobium extracts are prepared by extraction with a polar solvent such as water, ethanol, glycerin, glycols or mixtures thereof, preferably with water.

Preferably, the Epilobium extract according to the present invention are aqueous extracts. Such aqueous Epilobium extracts can be prepared by a process encompassing the steps of milling aerial parts such as the flowers, leafs and/or stems of the respective Epilobium species which preferably have preferably been dried beforehand, more preferably under hot air followed by extraction of the dried plants with a solvent, preferably with a mixture of ethanol/water, followed by removal of the ethanol e.g. by (vacuum)distillation to obtain the respective aqueous Epilobium extract.

Preferably, in all embodiments of the present invention the Epilobium fleischeri extract is an aqueous extract. Such aqueous Epilobium fleischeri extract can be prepared by a process encompassing the steps of milling aerial parts of Epilobium Fleischeri which preferably have preferably been dried beforehand, more preferably under hot air followed by extraction of the dried plants with a solvent, preferably with a mixture of ethanol/water, followed by removal of the ethanol e.g. by (vacuum)distillation to obtain the aqueous Epilobium fleischeri extract.

In all embodiments of the present invention said aqueous extract comprise an Epilobium extract, preferably an Epilobium fleischeri extract and may be admixed with further ingredients such as preferably glycerine, citric acid and preservative(s) such as potassium sorbate, e.g. before being used to be incorporated into a composition according to the present invention.

The Epilobium extract, preferably the Epilobium fleischeri extract according to the present invention provides microbiome balancing when applied on an external surface of the human body.

Because of the increase in the number of good bugs upon exposure to Epilobium extract, preferably Epilobium fleischeri extract, metabolites secreted by good bugs are also likely to increase. Without wishing to be bound by theory, these metabolites are believed to contribute to the natural-defense system of the human body.

Accordingly, in a further aspect, the present invention relates to use of an Epilobium extract, preferably Epilobium fleischeri extract for improving natural-defense system of an external surface of the human body by way of microbiome balancing.

Accordingly, in another aspect, the present invention relates to a method of improving natural-defense system of a surface of the human body by way of microbiome balancing comprising the step of applying an Epilobium extract, preferably an Epilobium fleischeri extract to the external surface of the human body.

The prebiotic effect according to the present invention is characterized by the fact that the differential abundance of at least one microbe, preferably all micobes selected from the group consisting of *Staphylococcus hominis, Staphylococcus epidermidis; Micrococcus yunnanensis; Cutibacterium*

*granulosum, Corynebacterium accolens* in the skin microbiome of an individual in need thereof is increased.

The prebiotic effect according to the present invention is preferably furthermore characterized by the fact that the differential abundance of at least one microbe, preferably all microbes selected from the group consisting of *Staphylococcus capitis; Corynebacterium tuberculostearicum; Lawsonella clevelandensis, Staphylococcus aureus* and *C. kroppenstedtii* in the skin microbiome of an individual in need thereof is decreased.

Therefore in a further aspect, the present invention also relates to the use of an Epilobium extract, preferably an Epilobium fleischeri extract respectively a topical composition comprising an Epilobium extract, preferably an Epilobium fleischeri extract for increasing the differential abundance of at least one microbe, preferably all microbes selected from the group consisting of *Staphylococcus hominis, Staphylococcus epidermidis; Micrococcus yunnanensis; Cutibacterium granulosum, Corynebacterium accolens* in the skin microbiome of an individual in need thereof. Preferably, the use encompasses the concomitant decrease in the differential abundance of at least one microbe, preferably of all microbes selected from the group consisting of *Staphylococcus capitis; Corynebacterium tuberculostearicum; Lawsonella clevelandensis, Staphylococcus aureus* and *C. kroppenstedtii*.

In a further embodiment, the present invention also provides a method for providing protection to an external surface of the human body by increasing the differential abundance of at least one microbe, preferably all microbes selected from the group consisting of *Staphylococcus hominis, Staphylococcus epidermidis; Micrococcus yunnanensis; Cutibacterium granulosum, Corynebacterium accolens*, said method comprising the step of topically applying an Epilobium extract, preferably an Epilobium fleischeri extract to said external surface.

The term external surface of the human body as used herein encompasses the skin as well as the scalp (including hair and axilla) and the oral cavity. Preferably, in all embodiments of the present invention the external surface of the human body treated according to the present invention is the face, neck and/or body skin, most preferably the face (including the (lateral) cheek, forehead, nose, chin).

The phrase "microbiome balancing" used herein preferably means maintaining a surface of the human body e.g. skin, scalp including hairs, axilla and oral cavity, in healthy and infection free condition. Microbiome balancing is obtained by way of Epilobium extract, preferably Epilobium fleischeri extract functioning as a prebiotic, i.e. preferentially promoting growth of good bugs over bad bugs, on a surface of the human body.

The term 'skin microbiome' as used herein refers to the group of microbes which colonize a defined skin area of an individual, such as e.g. the forehead, the forearm, the cheek or the scalp, without being limited thereto.

The term 'differential abundance' as used herein, refers to the logarithm of the fold change in abundance of a taxa between two conditions. This analysis method, giving differentials as output, allows to identify microbiome taxa associated with certain biological or clinical conditions. Differentials can be ranked and sorted from lowest to highest. These "rankings" give information on the relative associations of features with a given covariate (i.e. treatment or time).

The 'differential abundance' as used herein is determined by the use of a software called Songbird as outlined in Morton et al. (Nat. Commun., 2019. 10(1): p. 2719), which is included herein by reference, which allows to build a statistical model testing for differences between i.e. treatments and compute differentials starting from relative abundance data coming from 16S rRNA sequencing. The output is a file containing the ranks of the features for certain metadata categories. The higher the rank, the more associated it is with that category (i.e. treatment).

The term 'increase respectively decrease in the differential abundance' as used herein is defined as the increase respectively decrease of the differential abundance of a specific microbe when compared to the differential abundance on the respective symmetric skin area placebo-treated of the same individual.

In all embodiments of the present invention the Epilobium extract, preferably the Epilobium fleischeri extract is preferably administered in the form of a topical composition comprising an effective amount of the Epilobium extract, preferably the Epilobium fleischeri extract and a cosmetically acceptable carrier.

The term 'an effective amount' refers to an amount necessary to obtain the desired physiological effect. The physiological effect may be achieved by one application dose or by repeated applications. The dosage administered may, of course, vary depending upon known factors, such as the physiological characteristics of the particular composition comprising the Epilobium extract, preferably the Epilobium fleischeri extract and its mode and route of administration; the age, health and weight of the recipient; the kind of concurrent treatment; the frequency of treatment; and the effect desired and can be adjusted by a person skilled in the art.

Generally, the amount of the Epilobium extract, preferably the Epilobium fleischeri extract in the topical compositions according to the present invention is selected in the range from 0.001 to 10 wt %, more preferably from 0.01 to 8 wt %, even more preferably from 0.1 to 7 wt %, furthermore preferably from 0.1 to 5 wt % and still more preferably from 0.1 to 3 wt %, based on the total weight of the topical composition. Further suitable ranges are from 0.05 to 2 wt.-% and from 0.1 to 1 wt.-%.

In all embodiments of the present invention, the use can be therapeutic or non-therapeutic. Preferably, the use is however non-therapeutic, including cosmetic.

The term 'cosmetically acceptable carrier' (also referred to herein as carrier) refers to all vehicles/carriers conventionally used in topical cosmetic compositions, i.e. which are suitable for topical application to the keratinous tissue, have good aesthetic properties, are compatible with the actives present in the composition, and will not cause any unreasonable safety or toxicity concerns. Such carriers are well-known to one of ordinary skill in the art.

The exact amount of carrier will depend upon the actual level of the Epilobium extract, preferably the Epilobium fleischeri extract and of any other optional ingredients that one of ordinary skill in the art would classify as distinct from the carrier (e.g., other active ingredients)

In an advantageous embodiment, the topical compositions according to the present invention comprise from about 50% to about 99%, preferably from about 60% to about 98%, more preferably from about 70% to about 98%, such as in particular from about 80% to about 95% of a carrier, based on the total weight of the topical composition.

In a particular advantageous embodiment, the carrier consists furthermore of at least 40 wt.-%, more preferably of at least 50 wt.-%, most preferably of at least 55 wt.-% of water, such as in particular of about 55 to about 90 wt.-% of water.

The topical compositions according to the present invention are preferably prepared by admixing the Epilobium extract, preferably the Epilobium fleischeri extract with all the definitions and preferences as given herein with/into a cosmetically acceptable carrier.

The use of Epilobium extract, preferably Epilobium fleischeri extract according to the present invention may be therapeutic or non-therapeutic. Preferably, the use is non-therapeutic, i.e. for cosmetic application. Thus, preferably in all embodiments the topical compositions are cosmetic (non-therapeutic) compositions.

The term "cosmetic composition" as used in the present application refers to cosmetic compositions as defined under the heading "Kosmetika" in Rompp Lexikon Chemie, 10th edition 1997, Georg Thieme Verlag Stuttgart, New York as well as to cosmetic compositions as disclosed in A. Domsch, "Cosmetic Compositions", Verlag fur chemische Industrie (ed. H. Ziolkowsky), 4th edition, 1992.

Suitable composition according to the invention are leave-on or rinse-off products, and include any product applied to the human body.

The composition can be in the form of a liquid, lotion, cream, foam, scrub, gel, soap bar or toner, or applied with an implement or via a face mask, pad or patch. Non-limiting examples of such compositions include leave-on skin lotions and creams, shampoos, conditioners, shower gels, face wash's, body wash's, toilet bars, antiperspirants, deodorants, depilatories, lipsticks, foundations, mascara, sunless tanners and sunscreen lotions.

Preferred compositions according to the present invention are leave on compositions, more preferably in the form of an emulsion or a gel.

The compositions of the invention (including the carrier) may comprise conventional adjuvants and additives, such as preservatives/antioxidants, fatty substances/oils, organic solvents, silicones, thickeners, softeners, emulsifiers, anti-foaming agents, soaps, detergents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the compositions according to the invention may also comprise further cosmetically active ingredients conventionally used in cosmetic compositions. Exemplary active ingredients encompass UV-filters, agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

If the composition is an emulsion, such as in particular an O/W—, W/O—, Si/W—, W/Si—, O/W/O—, W/O/W— or a pickering emulsion, then the amount of the oily phase present in such cosmetic emulsions is preferably at least 10 wt.-%, such as in the range of 10 to 60 wt.-%, preferably in the range of 15 to 50 wt.-%, most preferably in the range of 15 to 40 wt.-%, based on the total weight of the composition.

In one embodiment, the compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art.

If the composition according to the invention is an O/W emulsion, then it contains advantageously at least one O/W— or Si/W-emulsifier selected from the list of, glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are polyalkylene glycol ethers, sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one 0/W, respectively Si/W emulsifier is preferably used in an amount of 0.5 to 10 wt. %, in particular in the range of 0.5 to 6 wt.-%, such as more in particular in the range of 0.5 to 5 wt.-%, such as most in particular in the range of 1 to 4 wt.-%, based on the total weight of the composition.

Particular suitable O/W emulsifiers to be used in the compositions according to the invention encompass phosphate ester emulsifiers such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate as well as polyalkylene glycol ethers such as in particular polyethylene stearyl ethers such as Steareth-2 and Steareth-21.

A particular suitable class of 0/W emulsifier to be used in the compositions according to the invention are polyalkyleneglycolethers. Particularly preferred 0/W emulsifier in all embodiments of the present invention are the stearyl ethers of polyethyleneglycol, such as most preferably Steareth-2

(Polyoxyethylen (2) stearylether) or Steareth-21 (Polyoxy-ethylen (21) stearylether) as well as mixtures thereof. Such polyalkyleneglycolethers emulsifiers are e.g. commercially available under the Brij tradename at Croda.

Particularly preferred gels according to the present invention comprise water, a thickener, such as preferably an acrylate thickener and optionally further ingredients. The water content in such gels is preferably >85 wt.-%, more preferably >90 wt.-%.

The topical compositions according to the present invention advantageously comprise a preservative. Particular suitable preservatives in all embodiments of the present invention are phenoxyethanol and ethylhexylglycerin as well as mixtures thereof. When present, the preservative is preferably used in an amount of 0.1 to 2 wt.-%, more preferably in an amount of 0.5 to 1.5 wt.-%, based on the total weight of the composition.

The compositions according to the invention in general have a pH in the range of 3 to 10, preferably a pH in the range of 4 to 8 and most preferably a pH in the range of 5 to 8. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The following examples are provided to further illustrate the compositions and effects of the present invention. These examples are illustrative only and are not intended to limit the scope of the invention in any way.

EXAMPLE

In vivo study to demonstrate the prebiotic effect on facial microbiome with the treatment of formulated Epilobium fleischeri extract Methodological setup: In a 28 days in vivo placebo-controlled clinical study, a light gel formulation containing 3% Epilobium fleischeri flower/leaf/stem extract as outlined in table 1 was applied two times per day on the face. Sebum level was measured before and after treatment to confirm the known sebum reducing effects from Epilobium fleischeri extract. In addition microbiome samples were collected from different facial sites (forehead, nose wing, front cheek, lateral cheek, and chin) at the study start and after 28 days of treatment. 16S rRNA sequencing were performed on the extracted DNA. The results obtained from the 16S rRNA sequencing were processed following the "reference frames" approach published by Morton et al. (Nat. Commun., 2019. 10(1): p. 2719). The method allows to assess microbiota changes and how these changes are associated with time and with the treatment. A software called Songbird is adopted to calculate differentials starting from relative abundance data coming from 16S sequencing.

TABLE 1

| | Base formulation (Placebo) | Active formulation |
|---|---|---|
| INCI Name | Wt.- % | Wt.- % |
| Aqua | Ad 100 | Ad 100 |
| ACRYLATES/C10-30 ALKYL ACRYLATE CROSSPOLYMER | 0.3 | 0.3 |
| PHENOXYETHANOL, ETHYLHEXYLGLYCERIN | 1.00 | 1.00 |
| GLYCERIN, AQUA, CITRIC ACID, POTASSIUM SORBATE, EPILOBIUM FLEISCHERI FLOWER/ LEAF/STEM EXTRACT | 0.00 | 3.00 |
| AQUA, SODIUM HYDROXIDE | add to pH 5.5 | |

Results: The differential values referred to time and treatment are reported in the table 2 and 3 below.

The column "sampling position" indicates where in the face the microbiome sample has been taken. The column "Intercept" indicates the starting point for each microorganism. A positive value means that the microorganism of interest was present to a certain extent on the skin before the evaluation. The column "Treatment" refers to if and to what extent a specific microorganism is associated with the active treatment. The values reported are the result of the differential made by the software by using placebo-valued samples as a reference. Therefore, a positive value indicates positive association with the active treatment whereas a negative value indicates a negative association by the treatment. The "Time" column, suggests how specific microorganisms are associated with time, independently of the treatment. A positive value means that the microbe tends to increase its abundance over time.

First of all we identified some species that were both positively associated by the treatment with the Epilobium fleischeri extract in comparison to the placebo treatment (i.e. control) but also are known to have a positive influence on the human skin microbiome. This is reflected in table 2 in the column "treatment" by a positive differential value and so we consider that the growth of the selected species were favoured by the treatment.

TABLE 2

| The "reference frames" analysis for positively regulated species | | | | |
|---|---|---|---|---|
| Sampling position | Intercept | Treatment | Time | Species |
| cheek | 1.27751447873 | 0.228874916708 | −0.544504983788 | St. hominis |
| Lateral cheek | 1.00349654700 | 0.4281320781321 | −0.1412418596446 | St. hominis |
| Forehead | 2.77272038213 | 0.561305068256 | 0.1242964515655 | St. epidermidis |
| chin | 2.57411628058 | 0.535163912442 | 0.1115589713056 | St. epidermidis |
| cheek | 1.841159364756 | 1.114582757032 | −1.101744516259 | C. accolens |
| nose | 1.821209192276 | 0.882371737239 | −0.2124683622470 | C. granulosum |
| chin | 0.886907866506 | 0.645104977753 | −0.2319768319527 | C. granulosum |
| forehead | 1.760498330510 | 1.141440681936 | −0.533702102843 | M. yunnanensis |

TABLE 2-continued

| | The "reference frames" analysis for positively regulated species | | | |
| --- | --- | --- | --- | --- |
| Sampling position | Intercept | Treatment | Time | Species |
| nose | 0.672707796096 | 0.596773041961 | −0.0134971428862 | *M. yunnanensis* |
| Lateral cheek | 1.871380229254 | 0.3884648294062 | −0.365194153040 | *M. yunnanensis* |
| chin | 0.767720511465 | 0.622249934342 | −0.3413930411140 | *M. yunnanensis* |

In addition, we identified species that were both negatively associated by the treatment with the Epilobium fleischeri extract in comparison to the placebo but also are known to have a negative or potentially pathogenic effect on human skin. This is reflected in table 3 in the column "treatment" by a negative differential value and so we consider that the growth of the selected species were inhibited or reduced by the treatment.

TABLE 3

| | The "reference frames" analysis for negatively regulated species | | | |
| --- | --- | --- | --- | --- |
| Sampling position | Intercept | Treatment | Time | Species |
| chin | 0.496266654043 | −0.788341727587 | 0.456276995440 | *St. aureus* |
| Lateral cheek | −1.881784062127 | −0.359959581413 | 0.452613364905 | *St. aureus* |
| Forehead | −0.552189781748 | −2.0443147497 | 1.476980599221 | *St. capitis* |
| nose | 0.638826131820 | −1.350470231297 | 0.690238678062 | *St. capitis* |
| cheek | −0.27501724046 | −1.892348726713 | 0.98837651454 | *St. capitis* |
| Lateral cheek | 1.065752167959 | −2.12423748663 | 0.506346736103 | *St. capitis* |
| chin | −0.073096940011 | −2.531250741812 | 0.4528431122501 | *St. capitis* |
| forehead | −0.301635696970 | −0.734252400872 | 0.610786321219 | *C. tuberculostearicum* |
| cheek | 1.215127489146 | −0.263423522436 | 0.2856835290132 | *C. tuberculostearicum* |
| Lateral cheek | 0.813133378286 | −0.403873512068 | 0.2306053079664 | *C. tuberculostearicum* |
| forehead | −1.370813801370 | −0.352221258161 | 0.960943194684 | *L. clevelandensis* |
| Lateral cheek | 2.490233559866 | −1.531859347143 | 0.508680719882 | *L. clevelandensis* |
| chin | 3.082652380972 | −0.631708529326 | 0.1671858554085 | *L. clevelandensis* |
| forehead | 5.019357249654 | −2.353590615270 | −0.704599050226 | *C. kroppenstedtii* |
| cheek | 4.014152667101 | −0.347485323869 | 0.0196722313104 | *C. kroppenstedtii* |
| Lateral cheek | 2.41402449156 | −0.708272525587 | −0.074208717793 | *C. kroppenstedtii* |

Thus, overall, considering the treatment-based results on the species listed in tables 2 and 3 as a group-result it clearly shows a shift of the microbiome to, for skin, a healthier composition since the growth and relative abundance of species with positive association to skin health are favoured and species with negative consequences on skin or pathogenic potential are reduced by the treatment. We therefore can conclude that the treatment promoted a specific regulation of species growth on one side and inhibition on the other side resulting in a positive rebalancing of the facial microbiome and this can be considered as a prebiotic effect resulting from the application of the Epilobium fleischeri extract.

The invention claimed is:

1. A method to increase the differential abundance of at least one microbe selected from the group consisting of *Staphylococcus hominis, Staphylococcus epidermidis; Micrococcus yunnanensis, Cutibacterium granulosum*, and *Corynebacterium accolens*, in the skin microbiome of an individual in need thereof, the method comprising the step of topically administering an effective amount of an Epilobium extract to an external surface of the individual in need thereof.

2. The method according to claim 1, wherein the method comprises simultaneously reducing the differential abundance of at least one microbe selected from the group consisting of *Staphylococcus capitis; Corynebacterium tuberculostearicum; Lawsonella clevelandensis, Staphylococcus aureus* and *Corynebacterium kroppenstedtii*.

3. The method according to claim 1, wherein the Epilobium extract is an Epilobium fleischeri extract, an Epilobium *Angustifolium* extract or an Epilobium *Parviflorum* extract.

4. The method according to claim 3, wherein the Epilobium extract is an Epilobium fleischeri extract.

5. The method according to claim 1, wherein the Epilobium extract is an aqueous extract obtained from the flowers, leaves and/or stems of an Epilobium plant.

6. The method according to claim 1, wherein the external surface of the individual in need thereof is at least one of skin, scalp, an axilla cavity and oral cavity.

7. The method according to claim 1, wherein the method comprises administering the Epilobium extract in the form of a topical composition comprising an effective amount of the Epilobium extract and a cosmetically acceptable carrier.

8. The method according to claim 7, wherein the topical composition comprises from 0.001 to 10 wt % of the Epilobium extract, based on the total weight of the topical composition.

9. The method according to claim 8, wherein the topical composition comprises from 0.1 to 5 wt % of the Epilobium extract, based on the total weight of the topical composition.

10. The method according to claim 8, wherein the topical composition is a leave-on composition.

11. The method according to claim 1, wherein the method is non-therapeutic.

12. A method for providing protection to an external surface of the human body by increasing the differential abundance of at least one microbe selected from the group consisting of *Staphylococcus hominis, Staphylococcus epidermidis, Micrococcus yunnanensis; Cutibacterium granulosum* and *Corynebacterium accolens* in the skin microbiome of an individual in need thereof, the method comprising the step of applying an Epilobium extract to the external surface of the individual in need thereof.

13. The method according to claim 12, wherein the method comprises simultaneously reducing the differential abundance of at least one microbe selected from the group consisting of *Staphylococcus capitis; Corynebacterium* tuberculostearicum; *Lawsonella* clevelandensis, *Staphylococcus aureus* and *Corynebacterium kroppenstedtii.*

14. The method according to claim 12, wherein the Epilobium extract is an Epilobium fleischeri extract, an Epilobium *Angustifolium* extract or an Epilobium *Parviflorum* extract.

15. The method according to claim 14, wherein the Epilobium extract is an Epilobium fleischeri extract.

16. The method according to claim 12, wherein the Epilobium extract is an aqueous extract obtained from the flowers, leaves and/or stems of an Epilobium plant.

17. The method according to claim 12, wherein the external surface of the human body in need thereof is at least one of skin, scalp, an axilla cavity and oral cavity.

18. The method according to claim 12, wherein the method comprises administering the Epilobium extract in the form of a topical composition comprising an effective amount of the Epilobium extract and a cosmetically acceptable carrier.

19. The method according to claim 18, wherein the topical composition comprises from 0.001 to 10 wt % of the Epilobium extract, based on the total weight of the topical composition.

20. The method according to claim 18, wherein the topical composition is a leave-on composition.

21. The method according to claim 12, wherein the method is non-therapeutic.

* * * * *